(12) United States Patent
Asfora (10) Patent No.: US 6,312,431 B1
(45) Date of Patent: Nov. 6, 2001

(54) VERTEBRAE LINKING SYSTEM

(76) Inventor: Wilson T. Asfora, 1500 W. 22nd St. Suite 101, Sioux Falls, SD (US) 57105

( * ) Notice: Subject to any disclaimer, the term of this patent is extended or adjusted under 35 U.S.C. 154(b) by 0 days.

(21) Appl. No.: 09/556,641

(22) Filed: Apr. 24, 2000

(51) Int. Cl.$^7$ .................................................. A61B 17/56
(52) U.S. Cl. ............................................................ 606/69
(58) Field of Search ................................. 606/61, 69, 70, 606/71; 623/17.15, 17.16, 17.11

(56) References Cited

U.S. PATENT DOCUMENTS

| | | | |
|---|---|---|---|
| 3,426,364 | * 2/1969 | Lumb | ................................ 623/17.15 |
| 4,047,523 | 9/1977 | Hall . | |
| 4,146,022 | 3/1979 | Johnson et al. . | |
| 4,583,541 | * 4/1986 | Barry | ....................................... 606/69 |
| 4,590,929 | 5/1986 | Klein . | |
| 4,790,303 | 12/1988 | Steffee . | |
| 4,828,562 | 5/1989 | Kenna . | |
| 4,896,668 | 1/1990 | Popoff et al. . | |
| 4,957,496 | 9/1990 | Schmidt . | |
| 4,966,142 | 10/1990 | Zimmerman et al. . | |
| 4,966,599 | * 10/1990 | Pollock | .................................. 606/69 |
| 5,108,397 | 4/1992 | White . | |
| 5,129,899 | 7/1992 | Small et al. . | |
| 5,151,104 | 9/1992 | Kenna . | |
| 5,234,431 | 8/1993 | Keller . | |
| 5,250,055 | 10/1993 | Moore et al. . | |
| 5,261,910 | 11/1993 | Warden et al. . | |
| 5,304,178 | 4/1994 | Stahurski . | |

(List continued on next page.)

OTHER PUBLICATIONS

Charles Dean Ray, "Neurosurgery Quarterly," Spinal Interbody Fusions: A Review, Featuring New Generation Techniques, Lippincott–Raven Publishers (Philadephia), vol. 7 (No. 2), p. 135–156, (Feb. 21, 1997).

Ole Bostman et al., "Acta Orthop Scand," Posterior spinal fusion using internal fixation with the Daab Plate, No. 55, p. 310–314, (Feb. 21, 1984).

O. Korlala et al., "Archives of Orthopaedic and Traumatic Surgery," Reduction and Fixation of late Diagnosed Lower Cervical Spine Dislocations Using the Daab Plate, Springer–Verlag, No. 103, p. 353–355, (Feb. 21, 1984).

*Primary Examiner*—Gene Mancene
*Assistant Examiner*—Eduardo C. Robert
(74) *Attorney, Agent, or Firm*—Kaardal & Associates, PC; Jeffrey A. Proehl (57) ABSTRACT

A vertebrae linking system for restricting relative movement between adjacent vertebrae and promoting fusion of the adjacent vertebrae. The invention comprises a system for linking spinous processes of adjacent vertebrae of a vertebral column of a patient, including an elongate linking plate apparatus for extending between the spinous processes of the adjacent vertebrae. The plate has opposite ends, and a pair of securing apertures formed in the linking plate, each of the securing apertures being located toward one of the ends of the linking plate. Preferably, a pair of sets of securing apertures are located at each end of the linking plate, each set of securing apertures comprising at least two apertures. The system includes a method for restricting movement of adjacent vertebrae with respect each other in the vertebral column of a patient, which comprises forming passages through the spinous processes, aligning securing apertures with the passages, and passing a connecting member through the apertures and passages. The system also includes a method for facilitating fusion between spinous processes of adjacent vertebrae, including forming an interstice between opposing faces of first and second plates and the spinous processes of first and second vertebrae, and placing a bone material in the interstice.

35 Claims, 5 Drawing Sheets

U.S. PATENT DOCUMENTS

| | | | |
|---|---|---|---|
| 5,352,224 | * 10/1994 | Westermann | 606/61 |
| 5,354,299 | 10/1994 | Coleman . | |
| 5,395,374 | 3/1995 | Miller et al. . | |
| 5,484,437 | 1/1996 | Michelson . | |
| 5,489,308 | 2/1996 | Kuslich et al. . | |
| 5,571,139 | 11/1996 | Jenkins, Jr. . | |
| 5,681,311 | * 10/1997 | Foley et al. | 606/61 |
| 5,702,397 | 12/1997 | Goble et al. . | |
| 5,722,976 | * 3/1998 | Brown | 606/69 |
| 5,741,253 | 4/1998 | Michelson . | |
| 5,766,254 | 6/1998 | Gelbard . | |
| 5,797,915 | 8/1998 | Pierson, III et al. . | |
| 5,797,916 | 8/1998 | McDowell . | |
| 5,810,825 | 9/1998 | Huebner . | |
| 5,947,965 | 9/1999 | Bryan . | |
| 5,947,966 | 9/1999 | Drewry et al. . | |
| 5,947,971 | 9/1999 | Kuslich et al. . | |
| 5,951,553 | 9/1999 | Betz et al. . | |
| 5,976,135 | 11/1999 | Sherman et al. . | |
| 5,980,523 | 11/1999 | Jackson . | |
| 5,984,922 | 11/1999 | McKay . | |
| 5,989,250 | 11/1999 | Wagner et al. . | |
| 5,989,256 | 11/1999 | Kuslich et al. . | |
| 6,152,927 | * 11/2000 | Farris et al. | 606/69 |

* cited by examiner

VERTEBRAE LINKING SYSTEM

BACKGROUND OF THE INVENTION

1. Field of the Invention

The present invention relates to spine stabilization and fusion systems and more particularly pertains to a new vertebrae linking system for restricting relative movement between adjacent vertebrae and promoting fusion of the adjacent vertebrae.

2. Description of the Prior Art

The spine of a person is comprised of a series of vertebra arranged in a vertebral column, and each of the vertebrae rests upon a lower vertebra in the vertebral column. Interposed between each pair of adjacent vertebrae is an intervertebral disc that permits a degree of movement of the adjacent vertebrae with respect to each other.

Surgical removal of one or more of the intervertebral discs may become necessary due to damage or deterioration of the discs. If the disc is wholly or partially removed, the spacing between the vertebra must be restored and maintained in the patient after removal in order to maintain the proper alignment and function of the spine.

Numerous techniques and instrumentations have been proposed and developed for restoring and maintaining the proper orientation of the vertebra after disc removal. One preferred procedure is interbody fusion which involves stimulating the fusion of the adjacent vertebrae with bone growth in the space previously occupied by the intervertebral disc. The fusing of the vertebrae with bone thus prevents the relative movement of the adjacent vertebrae that was previously possible with the presence of the disc. The fusing of the adjacent vertebrae in the vertebral column is a gradual process that can take a period of months to years. An important factor in achieving a faster and stronger fusion between the vertebrae is limiting the relative movement between the vertebrae during the period that the vertebrae are fusing together, until the completed vertebrae fusion prevents the relative movement therebetween.

One common technique for stimulating interbody fusion of adjacent vertebrae is the use of structures commonly referred to as "cages". These cage structures are inserted in between the vertebrae after the intervertebral disc has been wholly or partially removed. The surgical insertion of these cages may be performed either anteriorly or posteriorly. Typically, and especially in the case where substantially cylindrical cages are being employed, a portion of the face of each of the vertebrae is removed to form a seat for the cage. Significantly, the bone material removed from the vertebrae includes cancellous autologous bone material, which is typically inserted in the cage to stimulate the fusion of the vertebrae. The cancellous bone material is generally too soft to support and maintain the spacing between the vertebrae, but is highly suitable for stimulating the vertebral fusion when placed in a cage which secures the bone material and maintains the spacing between the vertebrae until fusion is complete.

However, the vertebrae adjacent to the interbody cage may still exhibit some relative movement prior to the fusion of the vertebral bodies together, which may slow down, and in some cases may even prevent, the vertebral interbody fusion from occurring. Various structures have been proposed and developed for attachment to posterior portions of the vertebrae, including the pedicle, the lamina, and the various processes protruding from the vertebral arch of the vertebra. These structures often include rods or plates which bridge between two or more vertebrae, and the rods and plates are typically attached to the vertebrae through the use of screws or cables.

The known structures are typically complex and bulky and require very invasive procedures to mount to the spine, especially when attached to laterally separated portions of the vertebrae such as the transverse and articular processes, and even the lamina and pedicle. Also, the known structures often need to be surgically removed at some future time.

In these respects, the vertebrae linking system according to the present invention substantially departs from the conventional concepts and designs of the prior art, and in so doing provides an apparatus primarily developed for the purpose of restricting relative movement between adjacent vertebrae and promoting fusion of the adjacent vertebrae.

SUMMARY OF THE INVENTION

In view of the foregoing disadvantages inherent in the known types of spine stabilization and fusion systems now present in the prior art, the present invention provides a new vertebrae linking system construction wherein the same can be utilized for restricting relative movement between adjacent vertebrae and promoting fusion of the adjacent vertebrae.

The general purpose of the present invention, which will be described subsequently in greater detail, is to provide a new vertebrae linking system which has many of the advantages of the spine stabilization and fusion systems mentioned heretofore and many novel features that result in a new vertebrae linking system which is not anticipated, rendered obvious, suggested, or even implied by any of the prior art spine stabilization and fusion systems, either alone or in any combination thereof.

To attain this, the present invention generally comprises a system for linking spinous processes of adjacent vertebrae of a vertebral column of a patient. The system includes an apparatus comprising an elongate linking plate for extending between the spinous processes of the adjacent vertebrae. The plate has opposite ends, and a pair of securing apertures formed in the linking plate, each of the securing apertures being located toward one of the ends of the linking plate. Preferably, a pair of sets of securing apertures are located at each end of the linking plate, with each set of securing apertures comprising at least two apertures. The system includes a method for restricting movement of adjacent vertebrae with respect each other in the vertebral column of a patient, which comprises forming passages through the spinous processes, aligning securing apertures with the passages, and passing a connecting member through the apertures and passages. The system also includes a method for facilitating fusion between spinous processes of adjacent vertebrae, including forming an interstice between opposing faces of first and second plates and the spinous processes of first and second vertebrae, and placing a bone material in the interstice.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new vertebrae linking system with an apparatus for linking spinous processes of adjacent vertebrae of a vertebral column of a patient, a method for restricting movement of adjacent vertebrae with respect each other in the vertebral column, and a method for facilitating fusion between spinous processes of adjacent vertebrae in the vertebral column.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

With reference now to the drawings, and in particular to FIGS. 1 through 12 thereof, a new vertebrae linking system embodying the principles and concepts of the present invention will be described.

As best illustrated in FIGS. 1 through 12, the vertebrae linking system generally comprises apparatus for linking spinous processes of adjacent vertebrae of a vertebral column of a patient, a method of employing the apparatus for restricting movement of adjacent vertebrae with respect each other, and a method of employing the apparatus for facilitating fusion between spinous processes of adjacent vertebrae.

The apparatus of the present invention includes an elongate linking plate 10 that is adapted for extending between the spinous processes of the adjacent vertebrae. The plate has opposite faces 14, 16, and opposite end edges 18, 20 extending between the opposite faces, and side edges 22, 24 extending between the opposite faces and between the end edges. The linking plate is preferably formed of a biocompatible material, such as, for example, titanium or a titanium alloy. Illustratively, one embodiment of the linking plate has a thickness between faces of approximately one-eighth inch (approximately 0.3 centimeters), and a width between side edges of 0.4 inches (approximately 1.1 centimeters).

In one highly preferred embodiment of the invention, the plate 12 has an arcuate configuration with the side edges 22, 24 of the plate being arcuate. One of the side edges 24 is concave and one of the side edges 22 is convex between the end edges. Ideally, each of the side edges have approximately the same radius of curvature. Illustratively, the convex side edge 22 may have a radius of curvature of approximately 9.5 inches (approximately 24 centimeters), and the concave side edge 24 may have a radius of curvature of approximately 9 inches (approximately 22.9 centimeters).

The linking plate 10 includes securing apertures for permitting securement of the plate to the spinous processes of adjacent vertebrae. The linking plate may be provided with a pair of securing apertures formed in the linking plate, with the apertures being separated from each other such that one of the apertures is located toward one end of the plate and the other of the apertures is located toward the other end of the plate. In one highly preferred embodiment of the linking plate, a pair of sets 28, 30 of securing apertures is provided in the linking plate, with each of the sets of securing apertures being located toward one of the ends 18, 20 of the linking plate such that the sets are separated from each other on opposite ends of the plate. Each set of securing apertures comprises at least two apertures positioned in relatively close proximity to each other. The grouping of at least two securing apertures in a set of apertures facilitates alignment of one of the securing apertures with a passage through one of the spinous processes without having to precisely measure the distance between the passages through the adjacent spinous processes and select a plate with a corresponding securing aperture spacing. In a highly suitable embodiment of the invention, each set of securing apertures includes three apertures in close proximity to each other. Optionally, each of the securing apertures of the sets may be positioned along an arc having substantially the same center of curvature as the arcuate side edges of the linking plate.

Illustratively, each of the securing apertures may have a diameter of approximately 0.1 inches (approximately 0.24 centimeters), and the spacing between adjacent securing apertures in a set may be approximately one eighth inch (approximately 0.3 centimeters), although spacing of up to approximately 0.15 inches (approximately 0.4 centimeters) or more may be used. The endmost aperture may be located away from the end of the plate approximately 0.15 inches (approximately 0.4 centimeters). The separation of the sets of securing apertures, as measured from the center of the set, may be approximately 1.02 inches (approximately 2.6 centimeters). The length of the linking member having two sets of securing apertures may be approximately 1.6 inches (approximately 4 centimeters).

A connecting member 34 is provided for connecting and securing the linking plate to the spinous process, and to a second linking plate in a preferred practice of the invention. In a highly preferred embodiment of the invention, the connecting member comprises an elongate flexible member 36 that is relatively thin for passing through the securing apertures (see FIG. 2). Illustratively, the elongate flexible member may comprise a cable formed of a plurality of strands, although the flexible member may comprise a wire, or any elongate flexible material with sufficient strength and biocompatibility. A loop 38 may be formed at one end of the flexible member for receiving the other end of the flexible member after the other end has been passed through the securing apertures and the spinous processes.

An embodiment of the linking plate that is highly suitable for use with the elongate flexible member includes securing apertures which are discrete from each other and thus are not in communication with each other (see FIGS. 1 through 4).

The elongate flexible member is highly preferred for use with the linking plates as insertion through the securing apertures and passages through the spinous processes tends to be easier than more rigid, threaded fasteners which typically a more precise alignment of the apertures and passages, and typically require significant rotation of the fasteners to tighten the threaded fasteners while in the surgical incision.

Optionally, the connecting member may comprise a rigid fastener 40 for securing the linking plate to the spinous processes. The rigid fastener comprises a head portion 42, a shaft portion 44, and a securing portion 46 removably mounted on the shaft portion (see FIG. 8). The rigid fastener 40 employed is preferably adapted for implantation in the body, and the head portion 42 may be provided with a recess adapted for receiving a hexagonal shaped tool, and the securing portion 46 may have radial recesses for receiving a tool to produce or prevent rotation of the securing portion with respect to the head and shaft portions.

Embodiment of the linking plate (FIGS. 5 and 6) that are highly suitable for use with the rigid fasteners have securing apertures that are each substantially circular, with a portion of each of the securing apertures overlapping one or more adjacent securing apertures. The overlapping apertures thus form a slot 48 having sides that have ridges 49 to limit movement of the fastener along the slot of the shaft portion. This feature permits the use of fasteners with shaft portions of relatively large diameter while permitting the centers of the securing apertures to be located relatively close to one another.

Figures 1, 3:
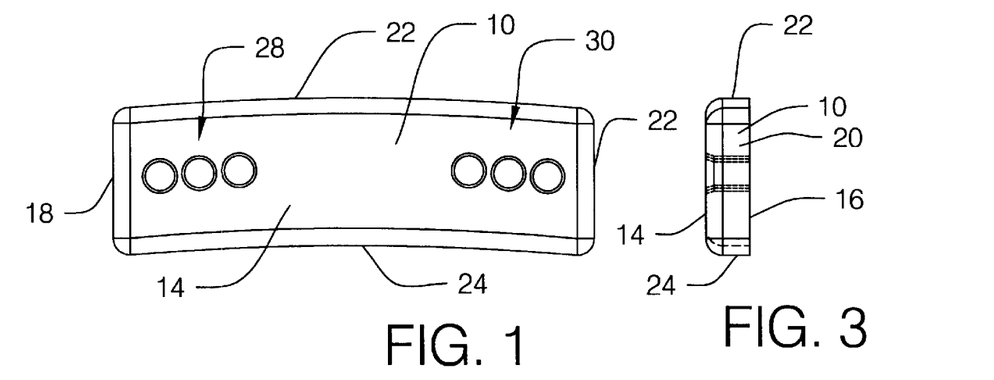
FIG. 1 is a schematic side view of a vertebrae linking plate of the present invention particularly adapted for linking two adjacent vertebrae of the vertebral column and particularly suited for use with an elongate flexible member.
FIG. 3 is a schematic end edge view of the linking plate.
Figure 2:
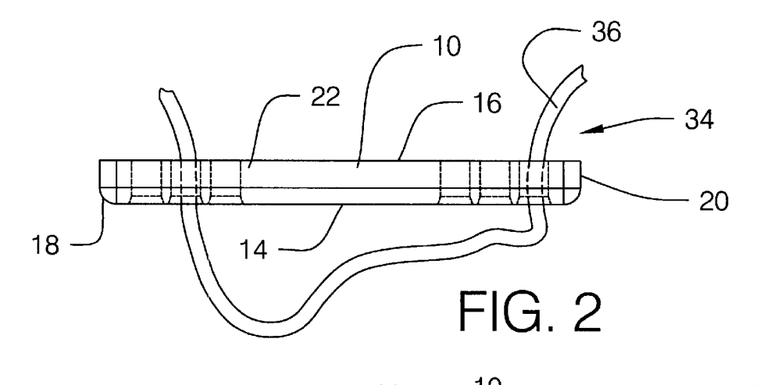
FIG. 2 is a schematic top side edge view of the linking plate.
Figure 4:
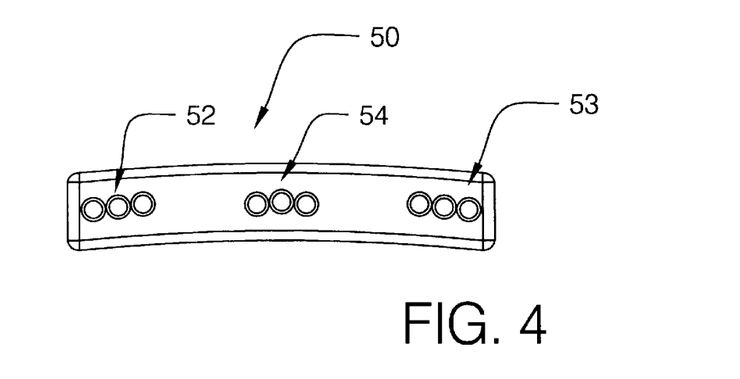
FIG. 4 is a schematic side view of a vertebrae linking plate of the invention adapted for linking three adjacent vertebrae of the vertebral column.
Figure 5:
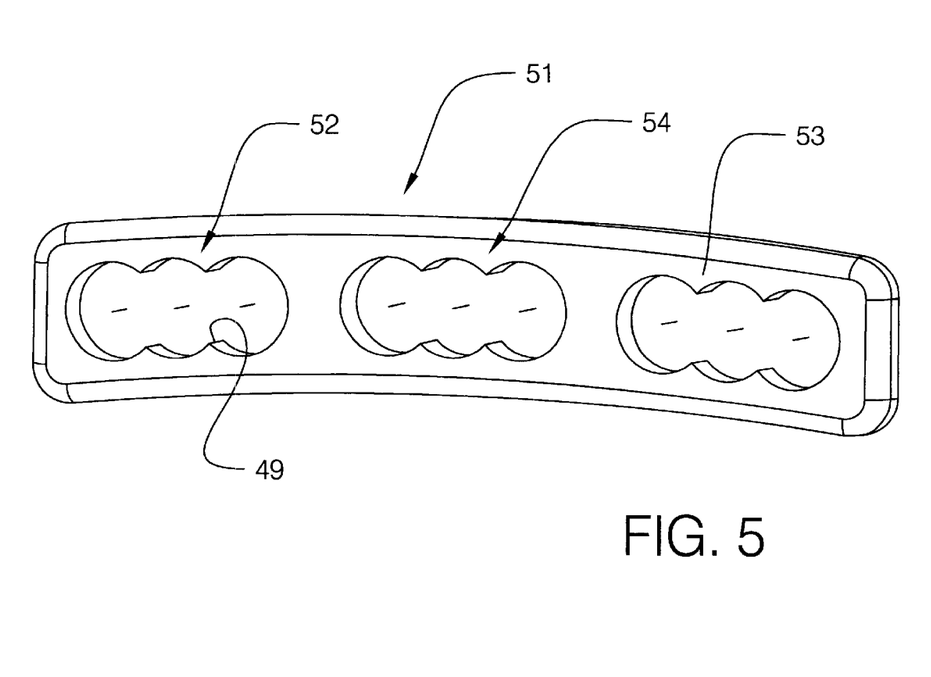
FIG. 5 is a schematic side perspective view of a linking plate of the invention particularly suitable for use with rigid fasteners.

In optional configurations 50, 51 of the linking plate, three sets of securing apertures are formed in the plate for permitting the linking of the spinous processes of three adjacent vertebrae (FIGS. 4 and 5). Preferably, a set 52, 53 of apertures is located toward each of the ends of the plate, and another set 54 is located approximately at a middle location between the ends. This embodiment of the plate is especially useful for use when, for example, two adjacent vertebral discs need to be replaced and the three adjacent vertebrae need to be linked.

Figure 6:
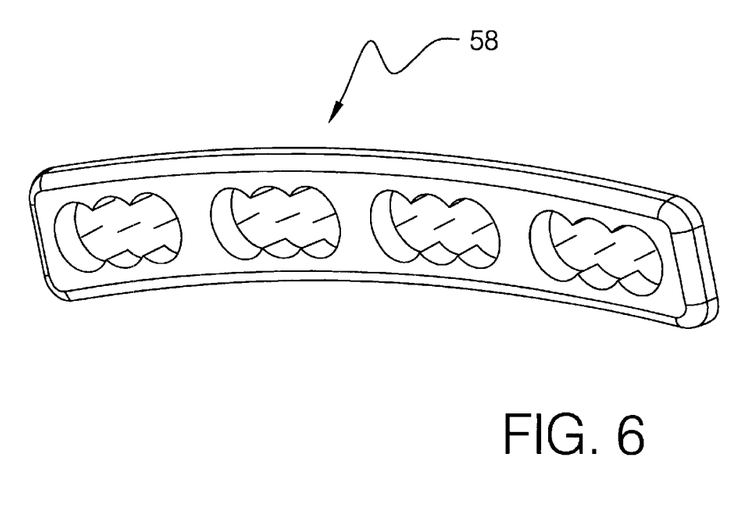
FIG. 6 is a schematic side perspective view of a linking plate of the present invention adapted for linking four adjacent vertebrae of the vertebral column.
Figures 7, 8:
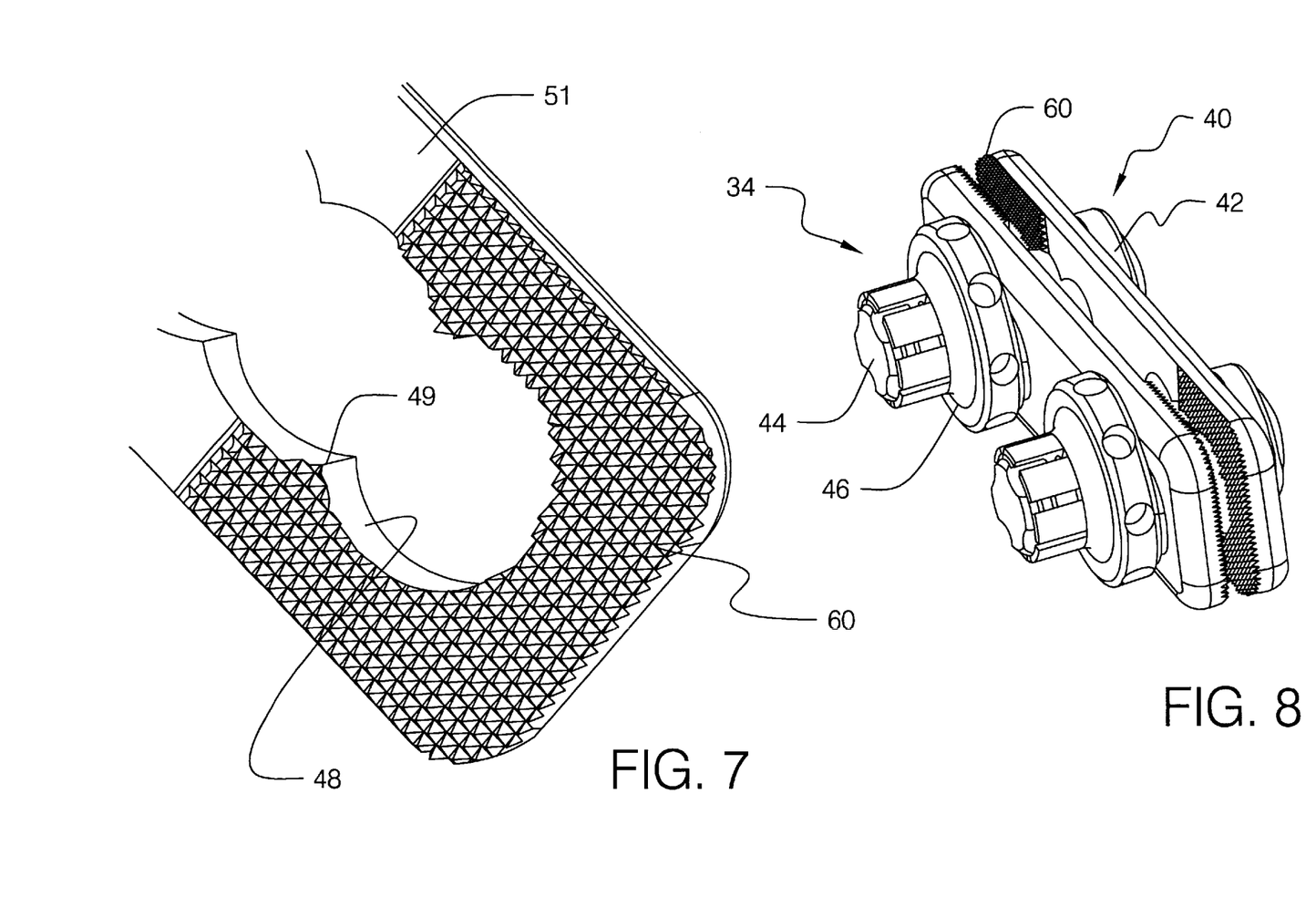
FIG. 7 is a schematic perspective view of a portion of an inner face of a linking plate particularly illustrating an optional roughened texture on the inner face.
FIG. 8 is a schematic end perspective view an optional embodiment of the linking plates of the present invention employing, rigid fasteners.

In another optional configuration 58 of the linking plate, four sets of securing apertures are formed in the plate for permitting the linking of the spinous processes of four adjacent vertebrae (FIG. 6). Preferably, one set of apertures is located toward each of the ends of the plate, and the remaining sets are located at approximately equal separations from the sets at the ends. This embodiment of the plate is especially useful for use when, for example, three adjacent vertebral discs need to be replaced and the four adjacent vertebrae need to be linked.

An optional feature of the linking plate is a roughened surface 60 (FIGS. 7 and 8) located on one of the faces of the plate that is to be oriented inward toward the spinous process for enhancing resistance to relative movement between the linking plate and the spinous process. The roughened surface may be limited to the end portions of the surface of the plate that are most likely to contact the spinous processes.

Figure 9:
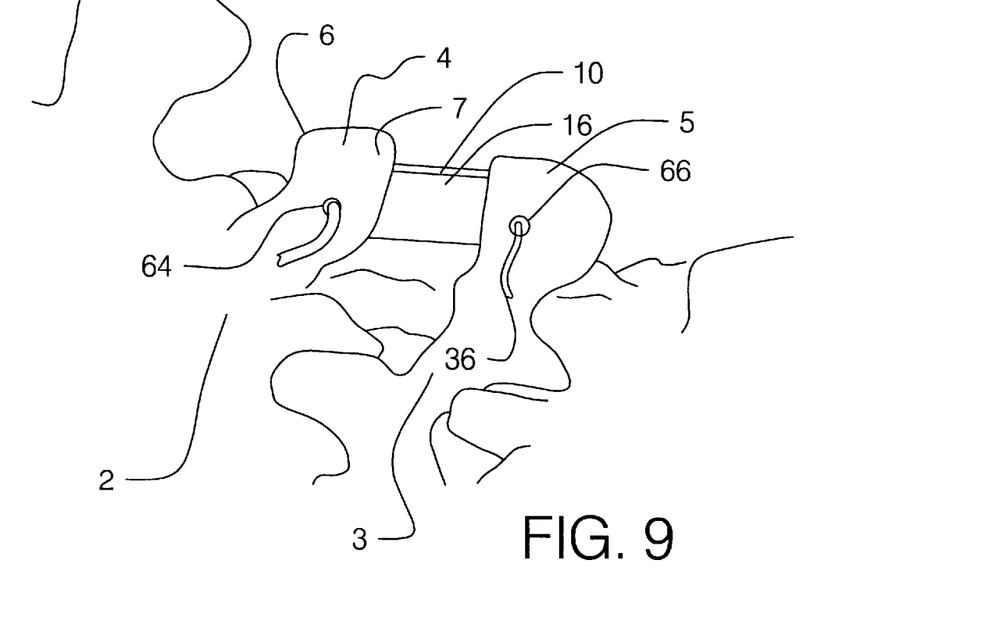
FIG. 9 is a schematic side perspective view of a linking plate of the invention mounted on the spinous processes of adjacent vertebrae in a medial view of the vertebral column, with one linking plate removed to show the passages through the spinous processes.
Figure 10:
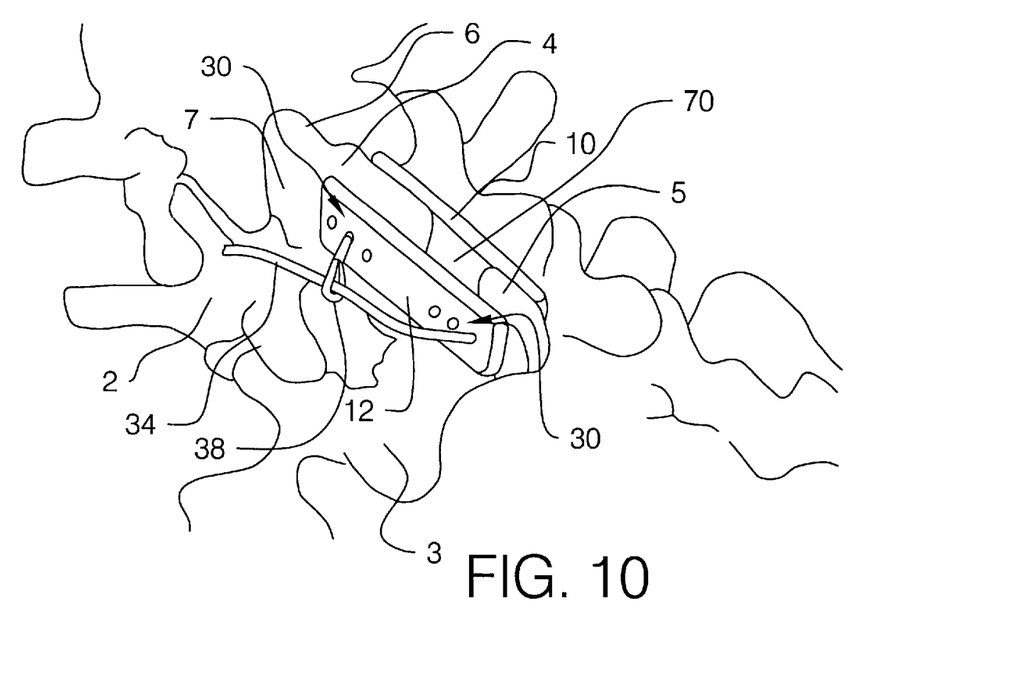
FIG. 10 is a schematic perspective view of the linking plates mounted on the spinous processes of adjacent vertebrae in a medial view of the vertebral column.
Figure 11:
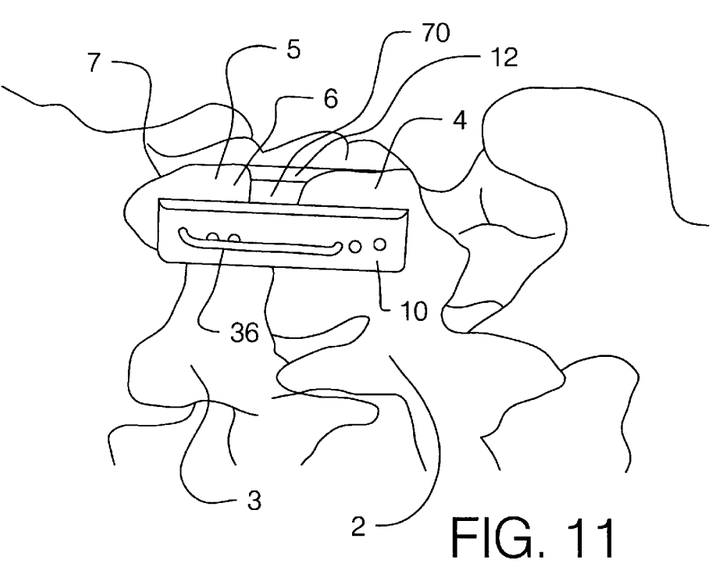
FIG. 11 is a schematic perspective view of the linking plates from an opposite medial perspective to that shown in FIG. 9.

The invention also includes a method for restricting movement of adjacent vertebrae with respect each other in the vertebral column of a patient using the linking plate of the invention (FIGS. 9 through 11). The method may be performed as part of or as a supplement to a surgical procedure to remove vertebral discs, especially when a vertebral interbody device, such as a cage, has been posteriorly inserted between the vertebrae of the patient.

Suitable vertebrae 2, 3 for use with the invention each have a spinous process 4, 5 extending posteriorly from the vertebral arch of the vertebra, and each of the spinous processes has first 6 and second 7 lateral surfaces.

The method includes surgically exposing the spinous processes of adjacent vertebrae for which movement is to be restricted relative to one another. The number of spinous processes to be exposed will depend upon the number of vertebrae to be restricted in movement.

A first passage 64 is formed through the spinous process of a first one of the adjacent vertebrae, and a second passage 66 is formed through the spinous process of a second one of the adjacent vertebrae. Each of the passages extends laterally through the spinous process between the lateral surfaces of the spinous process. The passage may be positioned at a substantially central location of the spinous process, although other positionings may be selected. The forming of the passage through the spinous process may be accomplished by various methods such as, for example, drilling or by punching. A preferred means for forming the passage through the processes is by the use of my spinous process punch, disclosed in my co-pending design patent application Ser. No. 29/105,950, filed Jun. 4, 1999.

A first linking plate 10 is placed against the first lateral surface 6 of each of the first 4 and second 5 spinous processes of the adjacent vertebra, and a second linking plate 12 is placed against the second lateral surface 7 of each of the first and second spinous processes of the adjacent vertebra. The first and second spinous processes of the first and second vertebrae are thus situated between the first and second plates, with the first and second spinous processes being spaced from each other to form an interstice 70 between the first and second plates and the spinous processes.

In a highly preferred practice that employs linking plates of the invention that have an arcuate shape, the curvature of the vertebral column at the location of the adjacent vertebra is determined, and the first and second linking plates are oriented such that the curvature of the linking plates generally corresponds to the curvature of the vertebral column at the location of the adjacent vertebrae. Thus, linking plates may be applied to vertebrae of the thoracic portion of the vertebral column such that a middle portion of the plate extends posteriorly. Similarly, linking plates may be applied to vertebrae of the cervical and lumbar portions of the vertebral column with the middle portion of the plate extending anteriorly.

One securing aperture of the first set of securing apertures of the first plate is substantially axially aligned with the first passage 64 extending through the spinous process of the first vertebra. Similarly, one securing aperture of the first set of securing apertures of the second plate is substantially axially aligned with the first passage extending through the spinous process of the first vertebra. The first passage 64 is thus substantially aligned with an aperture of the first set of securing apertures in each of the first and second linking plates.

A first connecting member is passed through the one (axially-aligned) securing aperture of the first set of the first plate and through the first passage of the spinous process of the first vertebra. The first connecting member is passed through the one (axially-aligned) securing aperture of the first set of the second plate, such that the securing apertures of the first and second plates are held in alignment with the first passage through the spinous process.

One securing aperture of the second set of securing apertures of the first plate is substantially axially aligned with the second passage extending through the spinous process of the second vertebra. One securing aperture of the second set of securing apertures of the second plate is substantially axially aligned with the second passage extending through the spinous process of the second vertebra. A second connecting member is passed through the one securing aperture of the second set of the first plate and the second passage of the second spinous process, and is passed through the second securing aperture of the second set of the second plate. In a preferred practice of the invention, the first connecting member and the second connecting member are formed by portions of a single continuous elongate flexible member.

The first connecting member is tightened such that the first and second plates are drawn toward each other with the first vertebra positioned therebetween. Similarly, the second connecting member is tightened such that the first and second plates are drawn toward each other with the second vertebra positioned therebetween. When the connecting member comprises an elongate flexible member 36, the tightening step includes cinching the elongate flexible member into a taut condition such that the flexible member resists the first and second plates moving away from an abutted condition against the spinous processes. The elongate flexible member is then secured in the taut condition with a clip or other securing means that holds portions of the flexible member together.

The invention also includes a method for facilitating fusion between spinous processes of adjacent vertebrae in the vertebral column of a patient. (FIG. 12) An interstice (FIG. 11) is formed between opposing faces of the first and second plates and between an inferior surface of the spinous process of an upper one of the first and second vertebrae and a superior surface of the spinous process of a lower one of the first and second vertebrae. The interstice 70 may be formed in the manner described above for mounting the plates on the spinous processes for resisting relative movement.

Figure 12:
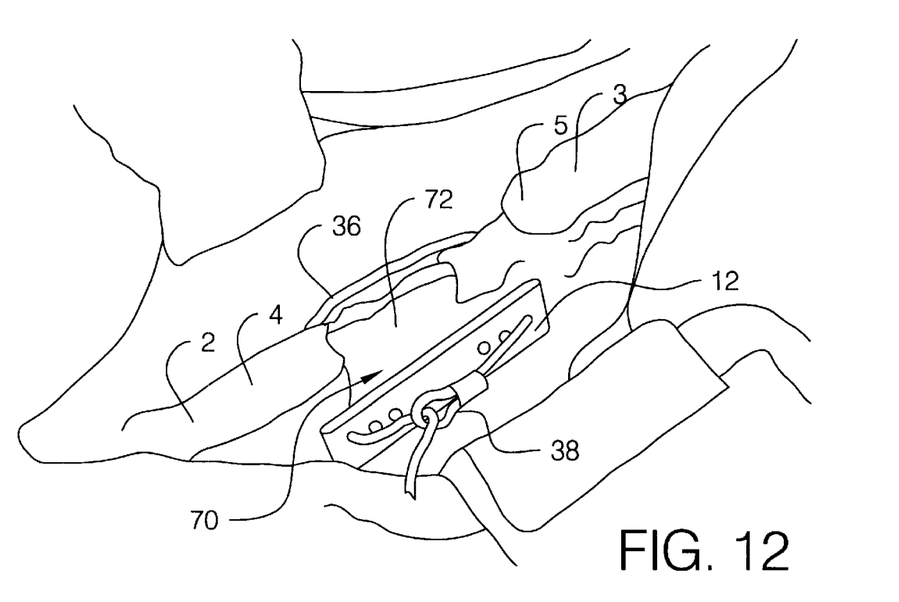
FIG. 12 is a schematic upper perspective view of a linking plate of the present invention in a surgical opening of the back of a patient and mounted on the spinous processes of the vertebral column and particularly illustrating the bone material positioned in the interstice between the linking plates.

Bone material 72, and most preferably cancellous bone material, may be removed from the vertebral body of one of the vertebra of the patient. The bone material removal may be accomplished as part of the insertion of interbody fusion cages between the vertebrae, such as by drilling across a face of the vertebral body or bodies for forming a seat for the interbody fusion cage.

The removed bone material 72 is placed in the interstice 70 formed by the linking plates, and preferably the bone material includes the cancellous bone material. The bone material may also be built up outside the interstice to enhance the size and strength of the future bone fusion area between the spinous processes.

Significantly, the linking plates and the connecting member may be left in place even after fusion of the bone material and the spinous processes has occurred, providing extra strength and rigidity to the bone fusion.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A system for linking spinous processes of adjacent vertebrae of a vertebral column of a patient, the system comprising:

an elongate linking plate for extending between the spinous processes of the adjacent vertebrae, the plate having opposite faces, opposite end edges, and side edges extending between the end edges, a pair of securing apertures formed in the linking plate, each of the securing apertures being located toward one of the ends of the linking plate such that the securing apertures are separated from each other on the plate, a portion of a surface of one of the opposite faces of the linking plate having greater roughness relative to a surface of the other of the opposite faces for resisting movement of the linking plate relative to a spinous process.

2. The system of claim 1 including a set of securing apertures located at each end of the linking plate, each set of securing apertures comprising at least two apertures.

3. The system of claim 2 wherein each set of securing apertures comprises three apertures in close proximity to each other.

4. The system of claim wherein the linking plate is arcuate between the ends.

5. The system of claim 4 wherein the side edges of the linking plate are arcuate, and wherein one of the side edges is concave and one of the side edges is convex.

6. The system of claim 5 wherein the side edges have approximately the same radius of curvature.

7. The system of claim 1 including a set of securing apertures located at each end of the linking plate, each set of securing apertures comprising at least two apertures, and wherein each of the securing apertures of the set is positioned along an arc.

8. The system of claim 1 additionally comprising an elongate flexible member for securing the linking plate to one of the spinous processes.

9. The system of claim 8 wherein the elongate flexible member comprises a cable.

10. The system of claim 1 including a set of securing apertures located at each end of the linking plate, each set of securing apertures comprising at least two apertures, wherein the securing apertures of each set are discrete from other securing apertures of the set.

11. The system of claim 1 including a set of securing apertures located at each end of the linking plate, each set of securing apertures comprising at least two apertures, wherein a portion of each of the securing apertures of a set overlaps an adjacent one of the securing apertures in the set such that the overlapping apertures of the set form a slot.

12. The system of claim 1 additionally comprising a rigid fastener for securing the linking plate to one of the spinous processes.

13. The system of claim 12 wherein the rigid fastener comprises a head portion, a shaft portion, and a securing portion removably mounted on the shaft portion.

14. The system of claim 1 including a set of securing apertures located at each end of the linking plate, each set of securing apertures comprising at least two apertures, wherein the linking plate has three sets of securing apertures formed therein for permitting the linking of the spinous processes of three adjacent vertebrae.

15. The system of claim 1 including a set of securing apertures located at each end of the linking plate, each set of securing apertures comprising at least two apertures, wherein the linking plate has four sets of securing apertures formed therein for permitting the linking of the spinous processes of four adjacent vertebrae.

16. The system of claim 1 wherein the surface of said one of the opposite faces has a pair of end portions separated by an intermediate portion, the intermediate portion having a relatively smooth surface and each of the end portions having a relatively roughened surface.

17. A method for restricting movement of adjacent vertebrae with respect each other in the vertebral column of a patient, each of the vertebrae having a spinous process extending posteriorly from the vertebral arch of the vertebra, each of the spinous processes having first and second lateral surfaces, the method comprising:

forming a first passage through the spinous process of a first one of the adjacent vertebrae, forming a second passage through the spinous process of a second one of the adjacent vertebrae, each of the passages extending laterally through the spinous process between the lateral surfaces of the spinous process;

providing first and second linking plates, each linking plate having opposite faces and opposite end edges, a pair of sets of securing apertures formed in the linking plate, each of the sets of securing apertures being located toward one of the ends of the linking plate such that the sets are separated from each other on the plate, each set of securing apertures comprising at least two apertures;

placing the first plate against the first lateral surface of each of the first and second spinous processes of the adjacent vertebra, placing the second plate against the second lateral surface of each of the first and second spinous processes of the adjacent vertebra;

substantially axially aligning one securing aperture of the first set of securing apertures of the first plate with the first passage extending through the spinous process of the first vertebra, and substantially axially aligning one securing aperture of the first set of securing apertures of the second plate with the first passage extending through the spinous process of the first vertebra;

passing a first connecting member through the one securing aperture of the first set of the first plate and the first passage of the spinous process of the first vertebra, passing the first connecting member through the one securing aperture of the first set of the second plate;

substantially axially aligning one securing aperture of the second set of securing apertures of the first plate with the second passage extending through the spinous process of the second vertebra, and substantially axially aligning one securing aperture of the second set of securing apertures of the second plate with the second passage extending through the spinous process of the second vertebra; and passing a second connecting member through the one securing aperture of the second set of the first plate and the second passage of the second spinous process, passing the second connecting member through the second securing aperture of the second set of the second plate.

18. The method of claim 17 additionally comprising the act of exposing the spinous processes of adjacent vertebrae to be stabilized with respect to each other.

19. The method of claim 18 wherein the first and second linking plates are each arcuate, and additionally comprising the act of positioning the plates such that the curvature of the plates generally corresponds to the curvature of the vertebral column at the location of the adjacent vertebrae.

20. The method of claim 17 additionally comprising the act of tightening the first connecting member such that the first and second plates are drawn toward each other with the spinous process of the first vertebra positioned therebetween, and tightening the second connecting member such that the first and second plates are drawn toward each other with the spinous process of the second vertebra positioned therebetween.

21. The method of claim 20 wherein the first connecting member and the second connecting member are formed by portions of a continuous elongate flexible member, and wherein the act of tightening includes cinching the elongate flexible member into a taut condition.

22. The method of claim 21 additionally comprising the act of securing the elongate flexible member in the taut condition.

23. A method for facilitating fusion between spinous processes of adjacent vertebrae in the vertebral column of a patient, each of the vertebra having a spinous process extending posteriorly from a vertebral arch of the vertebra, each of the spinous process having first and second lateral surfaces, the method comprising:

providing first and second linking plates, each linking plate having opposite faces and opposite end edges, a pair of sets of securing apertures formed in the linking plate, each of the sets of securing apertures being located toward one of the ends of the linking plate such that the sets are separated from each other on the plate, each set of securing apertures comprising at least two apertures;

placing the first plate against the first lateral surface of each of the first and second spinous processes of the adjacent vertebra, placing the second plate against the second lateral surface of each of the first and second spinous processes of the adjacent vertebra;

forming an interstice between opposing faces of the first and second plates and an inferior surface of the spinous process of an upper one of the first and second vertebrae and a superior surface of the spinous process of a lower one of the first and second vertebrae; and placing a bone material in the interstice.

24. The method of claim 23 additionally comprising the act of removing bone material from the vertebral body of one of the vertebra of the patient.

25. The method of claim 24 wherein the removing step includes drilling across a face of the vertebral body for forming a seat for an interbody fusion cage.

26. A system for linking spinous processes of adjacent vertebrae of a vertebral column of a patient, the system comprising:

a pair of elongate linking plates for extending between the spinous processes of the adjacent vertebrae, each plate having opposite faces, opposite end edges, and side edges extending between the end edges, a pair of securing apertures formed in each linking plate, each of the securing apertures being located toward one of the ends of each linking plate such that the securing apertures are separated from each other on the plate;

an elongate flexible member for securing the pair of linking plates to one of the spinous processes.

27. The system of claim 26 including a set of securing apertures located at each end of each linking plate, each set of securing apertures comprising at least two apertures;

wherein each linking plate is arcuate between the ends;

wherein the side edges of each linking plate are arcuate, and wherein one of the side edges is concave and one of the side edges is convex;

wherein the elongate flexible member comprises a cable; and wherein one of the faces of the linking plate has a pair of end portions separated by an intermediate portion, the intermediate portion having a relatively smooth surface and each of the end portions having a relatively roughened surface for resisting movement of the linking plate relative to a spinous process.

28. A method for restricting movement of adjacent vertebrae with respect each other in the vertebral column of a patient, each of the vertebrae having a spinous process extending posteriorly from the vertebral arch of the vertebra, each of the spinous processes having first and second lateral surfaces, the method comprising:

forming a first passage through the spinous process of a first one of the adjacent vertebrae, forming a second passage through the spinous process of a second one of the adjacent vertebrae, each of the passages extending laterally through the spinous process between the lateral surfaces of the spinous process;

providing first and second linking plates, each linking plate having opposite faces and opposite end edges, a pair of securing apertures formed in the linking plate, each of the securing apertures being located toward one of the ends of the linking plate such that the securing apertures are separated from each other on the plate;

placing the first plate against the first lateral surface of each of the first and second spinous processes of the adjacent vertebra, placing the second plate against the second lateral surface of each of the first and second spinous processes of the adjacent vertebra;

substantially axially aligning one securing aperture of the securing apertures of the first plate with the first passage extending through the spinous process of the first vertebra, and substantially axially aligning one securing aperture of the securing apertures of the second plate with the first passage extending through the spinous process of the first vertebra;

passing a first connecting member through the one securing aperture of the first plate and the first passage of the spinous process of the first vertebra, passing the first connecting member through the one securing aperture of the second plate;

substantially axially aligning one securing aperture of the securing apertures of the first plate with the second passage extending through the spinous process of the second vertebra, and substantially axially aligning one securing aperture of the securing apertures of the second plate with the second passage extending through the spinous process of the second vertebra; and passing a second connecting member through the one securing aperture of the second set of the first plate and the second passage of the second spinous process, passing the second connecting member through the second securing aperture of the second set of the second plate.

29. The method of claim 28 wherein the first and second linking plates are each arcuate, and additionally comprising the act of positioning the plates such that the curvature of the plates generally corresponds to the curvature of the vertebral column at the location of the adjacent vertebrae.

30. The method of claim 28 additionally comprising the act of tightening the first connecting member such that the first and second plates are drawn toward each other with the spinous process of the first vertebra positioned therebetween, and tightening the second connecting member such that the first and second plates are drawn toward each other with the spinous process of the second vertebra positioned therebetween.

31. The method of claim 28 wherein the first connecting member and the second connecting member are formed by portions of a continuous elongate flexible member.

32. The method of claim 31 wherein the act of tightening includes cinching the elongate flexible member into a taut condition, and additionally comprising the act of securing the elongate flexible member in the taut condition.

33. A method for facilitating fusion between spinous processes of adjacent vertebrae in the vertebral column of a patient, each of the vertebra having a spinous process extending posteriorly from a vertebral arch of the vertebra, each of the spinous process having first and second lateral surfaces, the method comprising:

providing first and second linking plates, each linking plate having opposite faces and opposite end edges, a pair of securing apertures formed in the linking plate, each of the securing apertures being located toward one of the ends of the linking plate such that the securing apertures are separated from each other on the plate;

placing the first plate against the first lateral surface of each of the first and second spinous processes of the adjacent vertebra, placing the second plate against the second lateral surface of each of the first and second spinous processes of the adjacent vertebra;

forming an interstice between opposing faces of the first and second plates and an inferior surface of the spinous process of an upper one of the first and second vertebrae and a superior surface of the spinous process of a lower one of the first and second vertebrae; and placing a bone material in the interstice.

34. The method of claim 33 additionally comprising the act of removing bone material from the vertebral body of one of the vertebra of the patient.

35. The method of claim 34 wherein the removing step includes drilling across a face of the vertebral body for forming a seat for an interbody fusion cage.

* * * * *